(12) United States Patent
Sotooka et al.

(10) Patent No.: US 8,139,842 B2
(45) Date of Patent: Mar. 20, 2012

(54) DEVICE AND METHOD FOR INSPECTING RECHARGEABLE BATTERY CONNECTION STRUCTURE

(75) Inventors: Sakae Sotooka, Toyohashi (JP); Fusayoshi Nomura, Toyohashi (JP)

(73) Assignee: Panasonic EV Energy Co., Ltd., Kosai-Shi, Shizuoka (JP)

(*) Notice: Subject to any disclaimer, the term of this patent is extended or adjusted under 35 U.S.C. 154(b) by 604 days.

(21) Appl. No.: 12/276,510

(22) Filed: Nov. 24, 2008

(65) Prior Publication Data

US 2009/0136115 A1    May 28, 2009

(30) Foreign Application Priority Data

Nov. 27, 2007    (JP) ................................. 2007-306273

(51) Int. Cl.
  *G06K 9/00*    (2006.01)
(52) U.S. Cl. .................... 382/141; 356/237.2; 356/237.6
(58) Field of Classification Search .................. 382/141, 382/149; 356/237.1–237.5
  See application file for complete search history.

(56) References Cited

U.S. PATENT DOCUMENTS

| | | | | |
|---|---|---|---|---|
| 3,560,093 A | * | 2/1971 | Montone | 356/393 |
| 5,907,396 A | * | 5/1999 | Komatsu et al. | 356/237.1 |
| 6,671,059 B2 | * | 12/2003 | Frisa et al. | 356/630 |
| 6,925,201 B2 | * | 8/2005 | Nakanishi et al. | 382/141 |
| 2002/0076094 A1 | * | 6/2002 | Nakanishi et al. | 382/141 |

FOREIGN PATENT DOCUMENTS

JP    2002-184386    6/2002

* cited by examiner

*Primary Examiner* — Gregory J Toatley
*Assistant Examiner* — Isiaka Akanbi
(74) *Attorney, Agent, or Firm* — Workman Nydegger

(57) ABSTRACT

An inspection apparatus for inspecting a rechargeable battery electrode plate-connected structure to check whether electrode plates are properly connected to a current collector plate by filters. The apparatus includes an imaging device arranged on one side of the rechargeable battery electrode plate-connected structure, a first lighting device which illuminates the rechargeable battery electrode plate-connected structure at the same side of the rechargeable battery electrode plate-connected structure as the first lighting device, a second lighting device which illuminates the rechargeable battery electrode plate-connected structure from the opposite side of the rechargeable battery electrode plate-connected structure, and an inspection circuit connected to the imaging device which inspects the connection state of the fillets by analyzing a front lighting image captured by the imaging device when only the first lighting device emits light and a back lighting image captured when only the second lighting device emits light.

12 Claims, 9 Drawing Sheets

DEVICE AND METHOD FOR INSPECTING RECHARGEABLE BATTERY CONNECTION STRUCTURE

CROSS-REFERENCE TO RELATED APPLICATIONS

This application claims the benefit of Japanese Patent Application No. 2007-306273, filed on Nov. 27, 2007, the entire contents of which are incorporated herein by reference.

BACKGROUND OF THE INVENTION

The present invention relates to a device and a method for optically inspecting a connection between a connecting end portion of an electrode plate and a current collector plate in a sealed rechargeable battery electrode plate-connected structure.

A sealed rechargeable battery or a secondary battery such as a nickel cadmium battery or a nickel metal hydride battery includes an electrolyte, a positive electrode plate-connected structure, and a negative electrode plate-connected structure, which are sealed in a battery case. The positive electrode plate-connected structure includes a plurality of rectangular positive electrode plates connected to a positive electrode current collector plate. The negative electrode plate-connected structure includes a plurality of rectangular negative electrode plates connected to a negative electrode current collector plate. The positive electrode plate and the negative electrode plate are alternately stacked one upon another. An insulative separator is arranged between adjacent electrode plates. Electrode plates having the same polarity are arranged in parallel at constant intervals. The electrode plates each have an edge (connecting end portion). In a state in which the edge is in contact with the associated current collector plate at a right angle, the electrode plate is brazed or welded and integrally connected to the current collector plate.

FIG. 10 shows connection portions of the electrode plates in one electrode plate-connected structure. As shown in FIG. 10, the electrode plate-connected structure includes a plurality of electrode plates 10, and a current collector plate 11. Flanges project from opposite ends of the current collector plate 11. The plurality of electrode plates 10 are arranged facing toward one another in a state spaced apart from one another. One edge (connecting end portion) of each electrode plate 10 is brazed or welded and connected to the surface of the current collector plate 11 (also referred to as current collector plate surface) at plural locations. In the example of FIG. 11, each electrode plate 10 is connected to the current collector plate 11 at five connection portions. At the connection portion of each electrode plate 10, brazing filler material covering the surface of the current collector plate 11 is melted and subsequently solidified to form a fillet 12. Thus, the current collector plates 11 are adhered to the major surface of the associated electrode plate 10 by the fillets 12. That is, the fillets 12 join the electrode plates 10 and the surface of the current collector plate 11.

Each fillet 12 is formed between two adjacent electrode plates 10 and between the outermost electrode plate 10 and the flange of the current collector plate 11. The fillet 12 is filled in a corner that is formed by the current collector plate 11 and the corresponding electrode plate 10 that is in contact with the current collector plate 11. Further, the fillet 12 has a depressed surface curved into a U-shape between the two adjacent electrode plates 10.

If the formation of some of the fillets 12 is incomplete, the connection strength of the electrode plate 10 to the current collector plate 11 may be insufficient. In such a case, the electrode plates 10 may be separated from the current collector plate 11 due to an impact or the like. The connection state of each electrode plate 10 and the current collector plate 11 is thus inspected before sealing the manufactured electrode plate-connected structure in an electrolytic cell.

Japanese Laid-Open Patent Publication No. 2002-184386 describes an inspection apparatus for optically inspecting the connection state of each electrode plate 10 and the current collector plate 11 of the rechargeable battery electrode plate-connected structure. The inspection apparatus captures an image of the connection portion between each electrode plate 10 and the current collector plate 11 in the electrode plate-connected structure, analyzes the captured image, and quantitatively evaluates the connection strength of each fillet 12 to determine whether or not the connection state of each electrode plate 10 and the current collector plate 11 is satisfactory. A prior art method for optically inspecting the connection state will now be described with reference to FIG. 11. An electrode plate-connected structure 100 is arranged between an imaging device 101 and a lighting device 102. The lighting device 102 illuminates the electrode plate-connected structure 100 as the imaging device 101 captures an image of the connection portion between each electrode plate 10 and current collector plate 11. In this case, inspection light is transmitted through the interior of the electrode plate-connected structure 100 and received by the imaging device 101, which captures an image of the electrode plate-connected structure 100.

SUMMARY OF THE INVENTION

When capturing an image with the inspection light transmitted through the electrode plate-connected structure 100, the inspection light may be shielded by when an electrode plate 10 has a bent portion. Such a bent portion would form a shadow and thereby hide a fillet 12. This would result in the fillet 12 being determined as missing, and the electrode plate-connected structure 100 would be erroneously determined as being defective. Such an erroneous decision can be avoided by raising the illuminance of the inspection light. However, if the illuminance of the inspection light is raised, halation may occur and interfere with the imaging of the electrode plate 10. This would rather adversely affect accurate inspection.

One aspect of the present invention is an inspection apparatus for a rechargeable battery electrode plate-connected structure including a plurality of electrode plates, each having a connecting end portion to be connected to a current collector plate by a fillet. The inspection apparatus is for inspecting a connection state of a fillet formed at a connection portion between each connecting end portion and the current collector plate. The inspection apparatus includes an imaging device arranged on one side of the rechargeable battery electrode plate-connected structure. A first lighting device emits inspection light to the rechargeable battery electrode plate-connected structure. The first lighting device is arranged on the one side of the rechargeable battery electrode plate-connected structure. A second lighting device emits inspection light to the rechargeable battery electrode plate-connected structure, with the second lighting device facing the imaging device so that the rechargeable battery electrode plate-connected structure is located between the second lighting device and the imaging device. An inspection circuit is connected to the imaging device. The inspection circuit inspects the connection state of the fillet by analyzing a front lighting image of the rechargeable battery electrode plate-connected structure, which is captured by the imaging device when only the first lighting device emits the inspection light, and a back lighting image of the rechargeable battery electrode plate-connected structure, which is captured when only the second lighting device emits the inspection light.

A further aspect of the present invention is a method for inspecting a rechargeable battery electrode plate-connected structure including a plurality of electrode plates, each having a connecting end portion to be connected to a current collector plate by a fillet. A connection state of a fillet formed at a connection portion between each connecting end portion and the current collector plate is inspected. The method includes illuminating one side of the rechargeable battery electrode plate-connected structure and capturing an image of the connection portion between each electrode plate and the current collector plate at a position facing toward the illuminated side of the rechargeable battery electrode plate-connected structure to acquire a front lighting image of the rechargeable battery electrode plate-connected structure, illuminating the rechargeable battery electrode plate-connected structure from one side of the rechargeable battery electrode plate-connected structure and capturing an image of the connection portion between each electrode plate and the current collector plate at a position facing toward a side of the rechargeable battery electrode plate-connected structure opposite the illuminated side to acquire a back lighting image of the rechargeable battery electrode plate-connected structure, and inspecting the connection state of the fillet by analyzing both the front lighting image and the back lighting image.

Other aspects and advantages of the present invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which.

DETAILED DESCRIPTION OF THE PREFERRED EMBODIMENTS

A preferred embodiment of a device and method for inspecting a rechargeable battery electrode plate-connected structure according to the present invention will now be discussed with reference to FIGS. 1 to 9. The illustrated inspection apparatus checks whether or not the connection state is satisfactory for the fillets 12 at the connection portion between the current collector plate 11 and electrode plates 10 in the rechargeable battery electrode plate-connected structure shown in FIG. 10.

Figure 1:
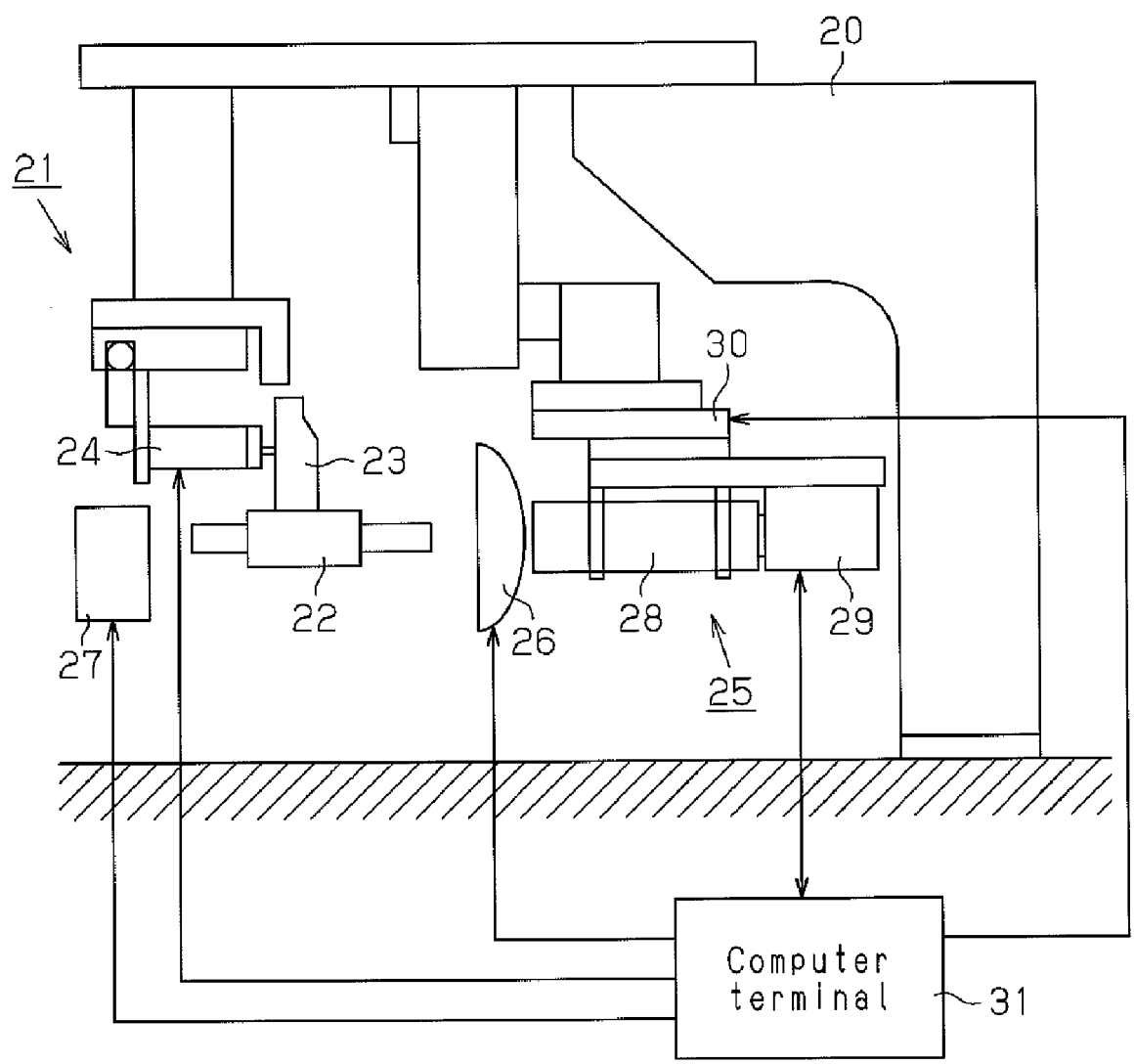
FIG. 1 is a schematic diagram showing an inspection apparatus for a preferred embodiment of a rechargeable battery electrode plate-connected structure according to the present invention.

As shown in FIG. 1, a work support 21 is supported by a frame 20 of the inspection apparatus. The work support 21 supports a pair of electrode plate-connected structures 22. The pair of electrode plate-connected structures 22 includes a positive electrode plate-connected structure, in which a plurality of positive electrode plates is connected to a current collector plate, and a negative electrode plate-connected structure, in which a plurality of negative electrode plates is connected to the current collector plate. The positive electrode plate-connected structure and the negative electrode plate-connected structure are joined so as to alternately stack the positive electrode plate and the negative electrode plate with an insulative separator arranged between the electrode plates. The work support 21 includes a chuck 23, which holds the pair of electrode plate-connected structures 22, and an adjustment mechanism 24, which moves the chuck 23 in a horizontal direction and a vertical direction and rotates the chuck 23 about a predetermined axis.

The frame 20 supports an imaging device 25 and a first lighting device 26, which are arranged on one side of the pair of electrode plate-connected structures 22 held by the work support 21. The frame 20 also supports a second lighting device 27, which is arranged facing toward the imaging device 25 with at the other side of the pair of electrode plate-connected structures 22. The first lighting device 26 and the imaging device 25 are arranged on the same side of the pair of electrode plate-connected structures 22. The second lighting device 27 is arranged at the opposite side of the pair of electrode plate-connected structures 22 from the imaging device 25. The imaging device 25 includes a telecentric lens 28, which collects incident light, and a CCD camera 29, which receives the light transmitted through the telecentric lens 28. An imaging device support 30 arranged on the frame 20 enables adjustment of the optical axes of the telecentric lens 28 and CCD camera 29 in any direction.

The first lighting device 26 and the second lighting device 27 each include a white LED (light source) and a white acrylic plate (diffuser plate). The inspection light generated by the white LED and emitted through the white acrylic plate irradiates the pair of electrode plate-connected structures 22. If only the first lighting device 26 is lit, the surface of the pair of electrode plate-connected structures 22 facing toward the imaging device 25 is irradiated by the inspection light. Therefore, the imaging device 25 receives a reflected light of the pair of electrode plate-connected structures 22. If only the second lighting device 27 is lit, the inspection light from the second lighting device 27 enters the pair of electrode plate-connected structures 22 parallel to the major surfaces of the electrode plate 10 (see FIG. 10). The imaging device 25 receives the inspection light that passes through gaps between the electrode plates 10 and along the surfaces of the electrode plates 10. Accordingly, when only the first lighting device 26 is lit, the imaging device 25 captures an image with the inspection light reflected by surface of the pair of electrode plate-connected structures 22 facing toward the imaging device 25. When only the second lighting device 27 is lit, the imaging device 25 captures an image with the inspection light passing through the gaps between the electrode plates 10 of the pair of electrode plate-connected structures 22.

The CCD camera 29 of the imaging device 25 is controlled by a computer terminal 31. The computer terminal 31 retrieves the image captured by the CCD camera 29, processes the image, and checks whether or not the connection state of the fillets 12 is satisfactory at the connection portion of the electrode plates 10 in the electrode plate-connected structure. The computer terminal 31 also controls the chuck 23 and the adjustment mechanism 24 of the work support 21 through a sequencer. The computer terminal 31 includes an input device, such as keyboard and mouse, and an output device, such as display (not shown).

The connection state inspection conducted on the fillets 12 in the rechargeable battery electrode plate-connected structure by the inspection apparatus will now be described in detail with reference to FIG. 2.

When a fillet inspection routine starts, in step S100, the computer terminal 31 first controls the adjustment mechanism 24 and arranges the pair of electrode plate-connected structures 22, which is held by the chuck 23, at a reference position. This positions the bottom surface of the current collector plate 11 of an electrode plate-connected structure at a reference position.

After the pair of electrode plate-connected structures 22 is arranged at the reference position, in steps S110 and S120, the computer terminal 31 controls the imaging device 25, the second lighting device 27, and the first lighting device 26 to capture and retrieve a back lighting image and a front lighting image of the rechargeable battery electrode plate-connected structure. That is, in step S110, in a state in which only the second lighting device 27 is lit, the computer terminal 31 captures an image of the connection portion of the electrode plates 10 in the electrode plate-connected structure with the CCD camera 29 and acquires image data of the back lighting image of the rechargeable battery electrode plate-connected structure. In step S120, in a state in which only the first lighting device 26 is lit, the computer terminal 31 captures an image of the connection portion of the electrode plates 10 in the electrode plate-connected structure with the CCD camera 29 and acquires the front lighting image of the rechargeable battery electrode plate-connected structure.

Figure 3A:
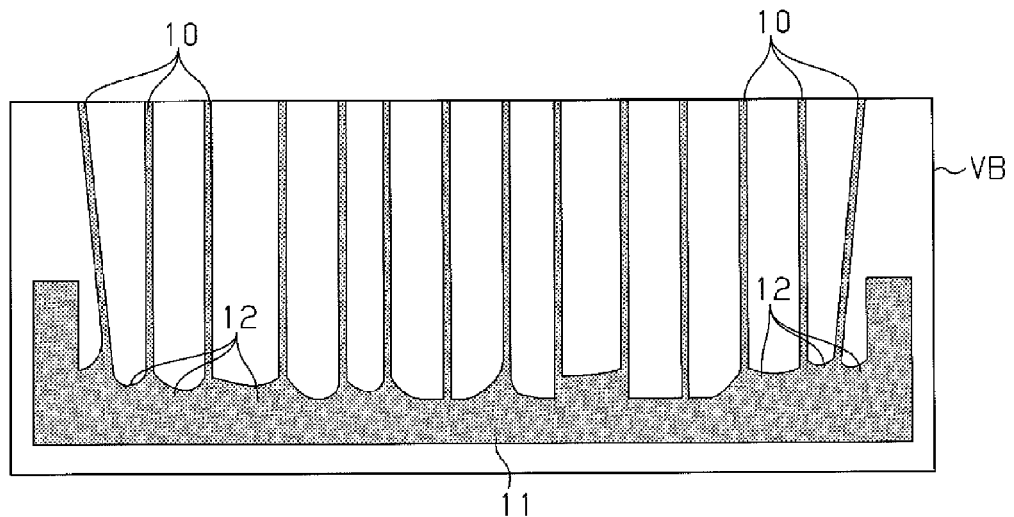
FIGS. 3(a) and 3(b) are diagrams respectively show a back lighting image and a front lighting image obtained in the fillet inspection routine of FIG. 2.
Figure 3B:
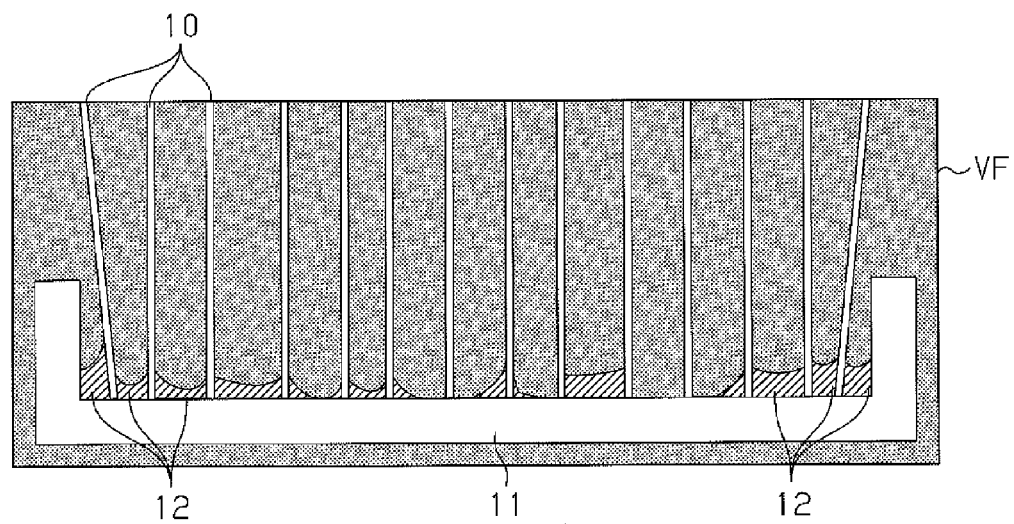
Figure 4A:
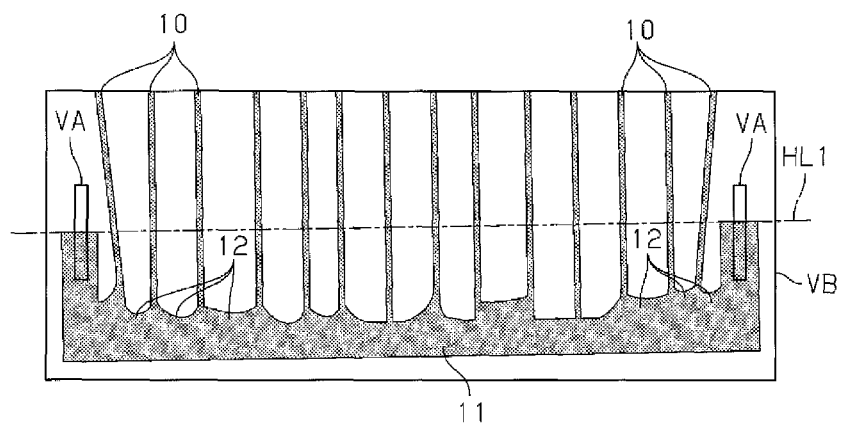
FIGS. 4(a) and 4(b) are diagrams respectively show a reference horizontal line HL1 obtained by using an upper end of a flange as a reference and a reference horizontal line HL2 obtained by using a current collector plate surface as a reference.
Figure 4B:
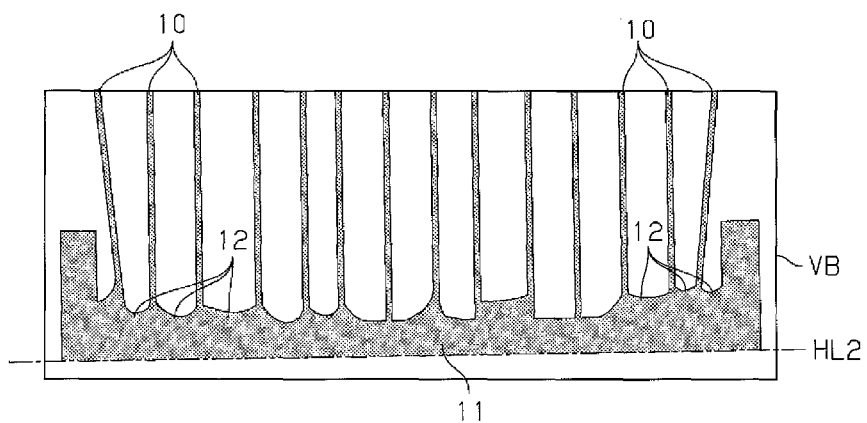

FIGS. 3(*a*) and 3(*b*) respectively show one example of a back lighting image VB and one example of a front lighting image VF. The back lighting image VB shown in FIG. 3(*a*) is captured in a state in which the pair of electrode plate-connected structures 22 is illuminated by the second lighting device 27. The second lighting device 27 and the imaging device 25 are located on opposite sides of the pair of electrode plate-connected structures 22 (see FIG. 1). Thus, the light that is transmitted through the electrode plate-connected structure without being shielded by the electrode plate-connected structure enters the CCD camera 29 as the inspection light. Therefore, in the back lighting image VB, the electrode plates 10, the current collector plate 11, and the fillets 12 formed at the connection portion between the electrode plates 10 and the current collector plate 11 of the electrode plate-connected structure appear in black as a silhouette, while other portions appear in white.

The front lighting image VF shown in FIG. 3(*b*) is captured in a state in which the pair of electrode plate-connected structures 22 is illuminated by the first lighting device 26. The pair of electrode plate-connected structures 22 and the imaging device 25 are located on the same side of the pair of electrode plate-connected structures 22 (see FIG. 1). Thus, the light reflected at the side of the electrode plate-connected structure facing toward the imaging device 25 enters the CCD camera 29 as the inspection light. Therefore, in the front lighting image VF, the side surfaces of the electrode plates 10 and the current collector plate 11 appear in white (bright), while other portions appear in black.

After retrieving the back lighting image VB and the front lighting image VF, in step S130, the computer terminal 31 checks whether a reference horizontal line should be obtained using a "flange reference" or a "current collector plate surface reference". The reference is used for the inspection is set in prior to the inspection. In the preferred embodiment, the reference horizontal line is obtained from the back lighting image VB regardless of which reference is used.

If the reference for obtaining the reference horizontal line is set to "flange reference", in step S140, the computer terminal 31 obtains a reference horizontal line HL1 using the flange reference. The reference horizontal line HL1 obtained from the flange reference will now be described with reference to FIG. 4(*a*). The computer terminal 31 sets measurement regions VA near the left and right ends of the back lighting image VB. In each measurement region VA, the grayscale of the image is sequentially calculated from top to bottom. A point at which a change in the grayscale becomes greater than or equal to a reference value is determined as being the upper end of each flange at the left and right ends of the current collector plate 11. A line connecting the upper ends of the two flanges is set as the reference horizontal line HL1. Depending on the current collector plate 11, the reference horizontal line HL1 may not be properly set due to the manufacturing tolerance allowed for the height of the two flanges. In this case, in step S150, the computer terminal 31 determines whether or not the reference horizontal line HL1 has been properly set. If the reference horizontal line HL1 has been properly set (OK), the computer terminal 31 proceeds to step S160. If the reference horizontal line HL1 has not been properly set (NG), the computer terminal 31 outputs a "reference line error signal" and immediately terminates the present inspection.

When the pair of electrode plate-connected structures 22 is arranged at the reference position in step S100, the bottom surface of the current collector plate 11 is arranged at the reference position. If the reference horizontal line is obtained based on the "current collector plate surface reference", the computer terminal 31 sets a line that coincides with the bottom surface of the current collector plate 11 in the back lighting image VB as a reference horizontal line HL2 (see FIG. 4(*b*)). The manufacturing tolerance allowed for the plate thickness of the current collector plate 11 is significantly small. Thus, the manufacturing tolerance does not cause the reference horizontal line HL2 to become improper. Accordingly, the computer terminal 31 sets the reference horizontal line HL2 and proceeds to step S160 without determining whether the reference line is proper.

The reference horizontal line HL1 or HL2 is set using either one of the references in the above manner. The set reference horizontal line HL1 or HL2 is used as the reference position in a flange height direction of the current collector plate 11 in the electrode plate-connected structure. In the description hereafter, a direction parallel to the reference horizontal line HL1 or HL2 is referred to as the X direction, and a direction perpendicular to the reference horizontal line HL1 or HL2 is referred to as the Y direction.

Figure 2:
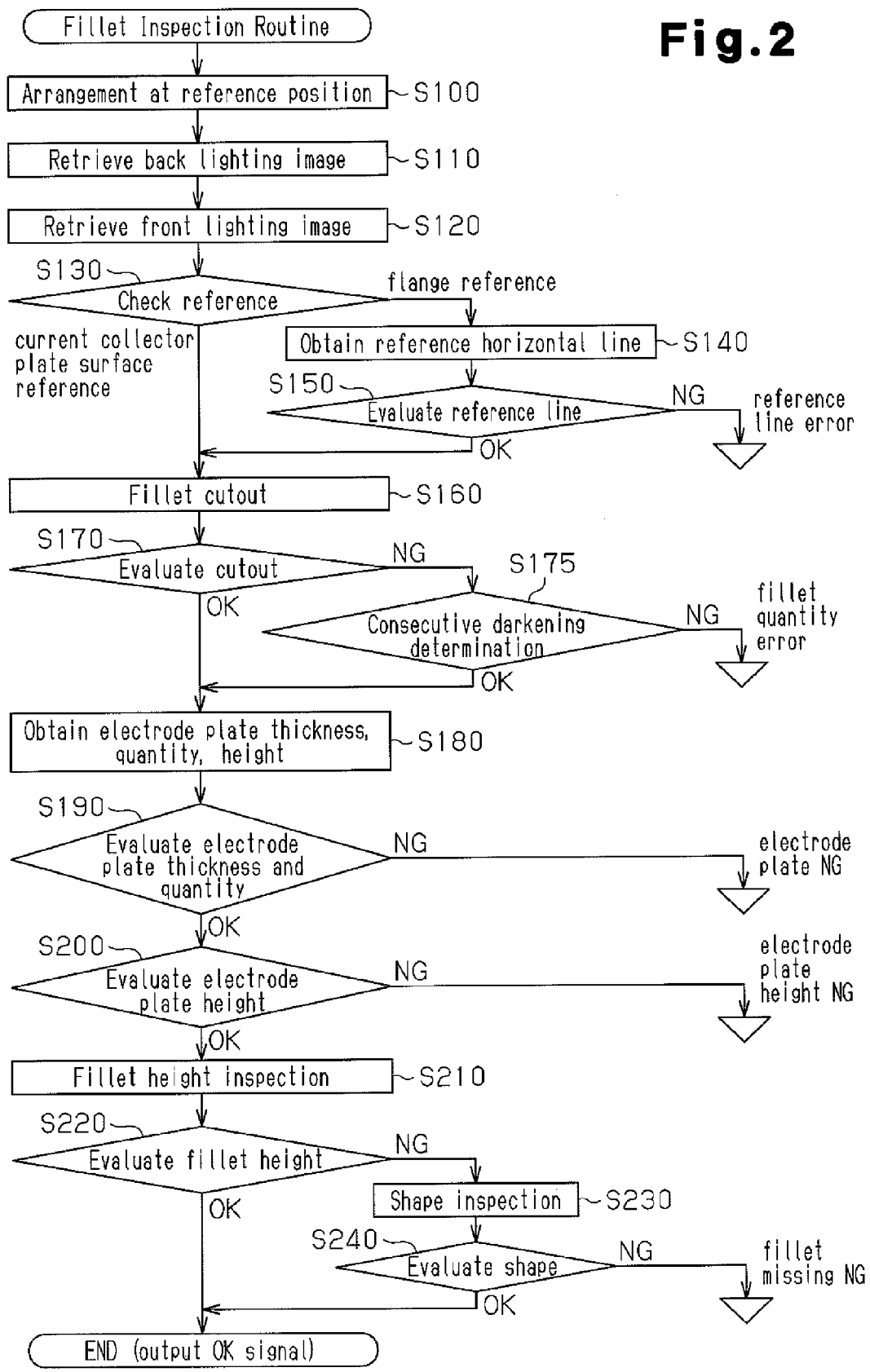
FIG. 2 is a flowchart illustrating a fillet inspection routine for the preferred embodiment.

In step S160 of FIG. 2, the computer terminal 31 performs a process for cutting out images of the fillets 12. The image cutout process of the fillets 12 will now be described with reference to FIGS. 5(a) to 5(c).

Figure 5A:
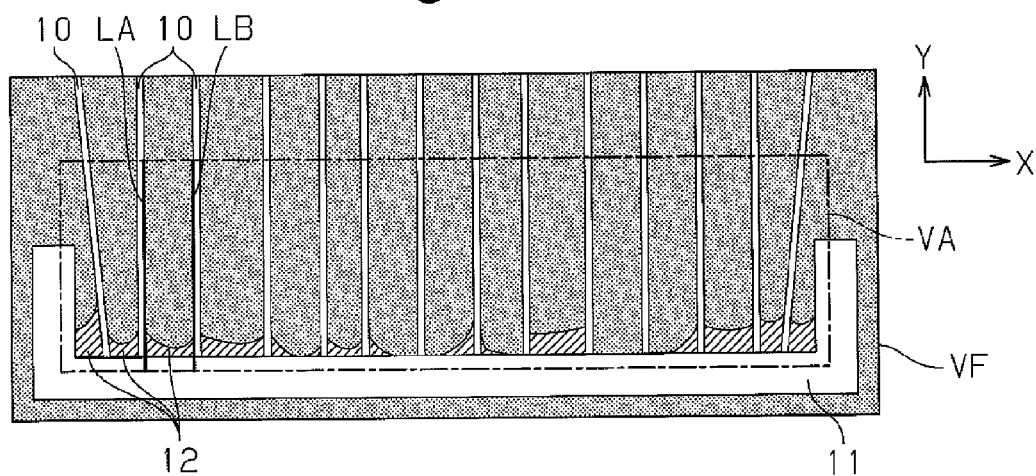
FIGS. 5(a) to 5(c) are diagrams illustrating a process for cutting out fillets.

As shown in FIG. 5(a), the computer terminal 31 first sets a rectangular range having fixed dimensions from the reference horizontal line HL1 or HL2 of the front lighting image VF as the measurement region VA. The computer terminal 31 detects X direction positions of the two major surfaces of each electrode plate 10 that appear in white in the front lighting image VF from the measurement region VA. In FIG. 5(a), the opposing surfaces of the second electrode plate 10 from the left and the third electrode plate 10 from the left are each marked with bold lines LA and LB.

Figure 5B:
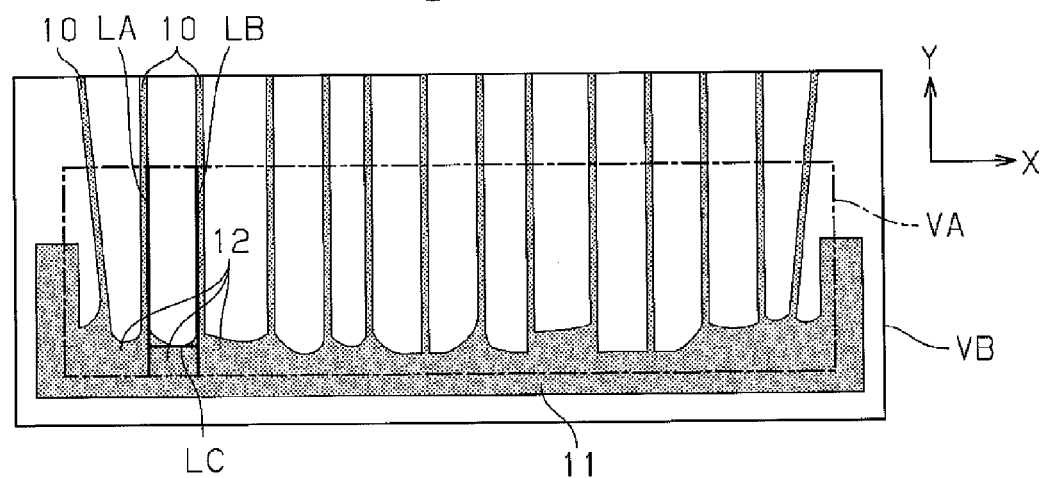

Then, as shown in FIG. 5(b), in the back lighting image VB, the computer terminal 31 detects the Y direction position of the boundary between the illuminated portion, which is between the electrode plates 10 and appear in white, and the silhouetted portion of the fillet 12, which appears in black, from the measurement region VA. In FIG. 5(b), the boundary in the gap between the second electrode plate 10 from the left and the third electrode plate 10 from the left is marked by bold line LC.

Figure 5C:
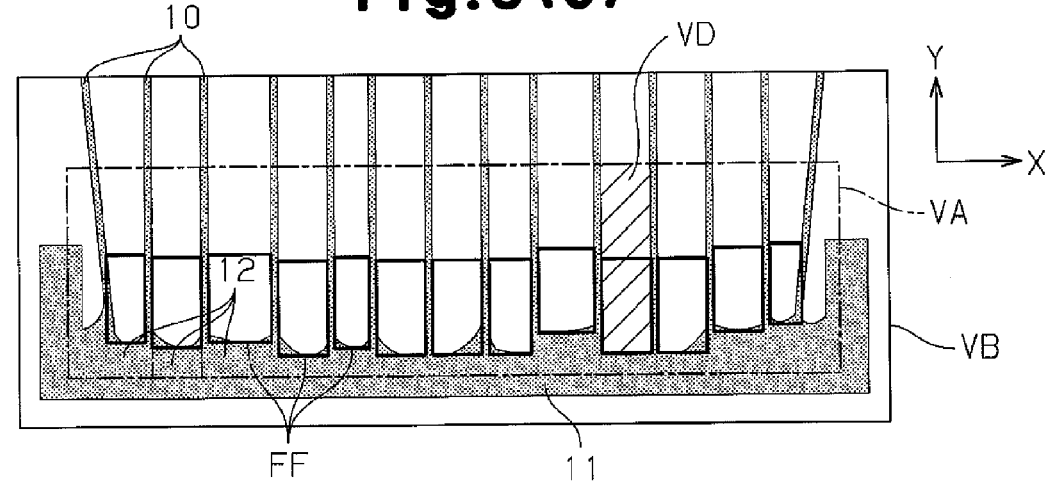

As shown in FIG. 5(c), the computer terminal 31 sets a rectangular region VD for each gap between the opposing electrode plates 10. The region denoted by reference character VD in FIG. 5(C) is rectangular. However, regions VD for other gaps may be trapezoidal. Each rectangular region VD includes first and second sides respectively corresponding to the opposing major surfaces of the two adjacent electrode plates 10, a lower side corresponding to the boundary line LC between the electrode plates 10, and an upper side corresponding to the upper side of the measurement region VA. In each rectangular region VD, the lower 50% in area is extracted. A rectangle extending around the extracted portion, that is, a circumscribing rectangle is set as a fillet cutout frame FF. A fillet cutout frame FF is set in each gap between the electrode plates 10.

After setting the fillet cutout frames FF, in step S170, the computer terminal 31 obtains the quantity of fillets 12 in the image from the quantity of the fillet cutout frames FF. The computer terminal 31 determines whether or not the obtained quantity of the fillets 12 is proper (cutout determination). If the quantity of the fillets 12 is proper (OK), the computer terminal 31 proceeds to step S180.

Figure 6:
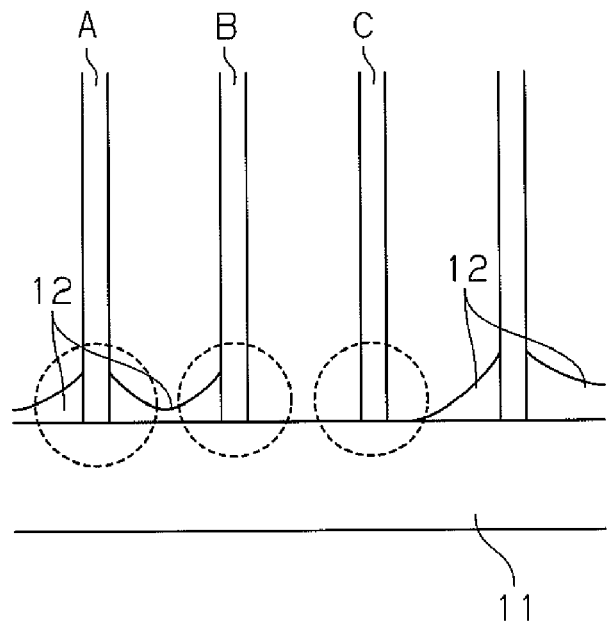
FIG. 6 is a diagram showing an example of the shape of the fillets.

If the quantity of the fillets 12 is not proper (NG), in step S175, the computer terminal 31 performs consecutive darkening determination. "Darkening" refers to a situation in which a portion between the electrode plates 10 is shadowed due to a bending or the like in the electrode plate 10, and a fillet cutout frame FF thus cannot be set between the adjacent electrode plates 10. "Consecutive darkening" refers to a situation in which two or more consecutive fillet cutout frames FF cannot be set in the X direction. In step S175, if there is even at least one consecutive darkening (NG), the computer terminal 31 outputs a "fillet quantity error signal" and immediately terminates the present inspection. If there is no consecutive darkening (S175: OK) even though the quantity of the fillets 12 is not proper (S170: NG), the computer terminal 31 proceeds to step S180 and continues the inspection. In other words, in the preferred embodiment, the inspection is continued even if there is a location in which a fillet cutout frame FF cannot be set as long as a fillet cutout frame FF can be set on each side of that location between electrode plates 10. Such a state is referred to as sole darkening If there is no consecutive darkening, that is, if there is only sole darkening, the inspection is continued for the following reasons. In FIG. 6, fillets 12 are properly formed on the two major surfaces of an electrode plate A. In this case, the strength for connecting the electrode plate A to the current collector plate 11 is sufficiently ensured. Further, in FIG. 6, a fillet 12 is not formed on the right major surface of an electrode plate B the right side but properly formed only on the left major surface. In this case, even though a fillet 12 is formed only on one side of the electrode plate B, sufficient strength for connecting the electrode plate B to the current collector plate 11 is ensured as long as the fillet 12 is properly formed. Proper fillets 12 are not formed on the two major surfaces of an electrode plate C. Such a state is referred to as a "fillet missing state", and the strength for connecting the electrode plate C to the current collector plate 11 is insufficient. As described above, the fillet missing state of electrode plate C must be determined as a state in which there is a connection strength defect.

Figure 7A:
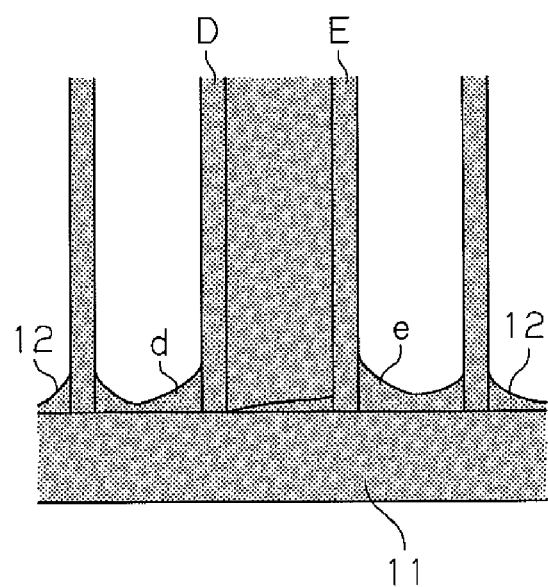
FIG. 7(a) is a diagram showing a back lighting image including a sole darkening.
Figure 7B:
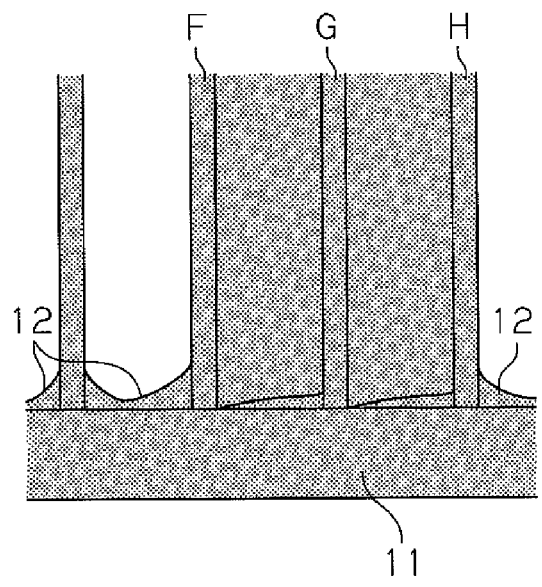
FIG. 7(b) is a diagram showing a back lighting image including consecutive darkening.

FIG. 7(a) shows an example of a back lighting image VB including sole darkening. FIG. 7(b) shows an example of a back lighting image VB including consecutive darkening. In the state of FIG. 7(a), the portion between adjacent electrode plates D and E forms a shadow. Thus, a fillet cutout frame FF cannot be set in this portion. In this case, a fillet on the right side of the electrode plate D and a fillet on the left side of the electrode plate E cannot be recognized. However, a fillet d on the left side of the electrode plate D and a fillet e on the right side of the electrode plate E are recognized. Thus, if the fillets d, e are properly formed, it can be determined that the strength connecting the electrode plate D and the electrode plate F to the current collector plate 11 is sufficiently ensured. That is, in this case, the strength connecting the electrode plate D and the electrode plate E to the current collector plate 11 can be evaluated.

In the state of FIG. 7(b), the portion between adjacent electrode plates F and G, and the portion between adjacent electrode plates G and H form consecutive shadows, and fillet cutout frames FF cannot be set in these two portions. In this case, it cannot be determined whether or not a fillet is formed on one or two sides of electrode plate G, which is located between two darkened portions. Thus, the strength connecting the electrode plate G to the current collector plate 11 cannot be evaluated.

In this manner, even if the obtained quantity of the fillets 12 is not proper, the strength connecting each electrode plate 10 to the current collector plate 11 can be evaluated as long as consecutive darkening is not recognized. The inspection is interrupted only if consecutive darkening is recognized, and the inspection is continued as long as only sole darkening is recognized.

Returning to FIG. 2, after step S170 or S175, the computer terminal 31 obtains the thickness and height of each electrode plate 10 and the quantity of the electrode plates 10 in step S180. The thickness, height, and quantity of the electrode plates 10 may be obtained from the front lighting image VF.

Figure 8A:
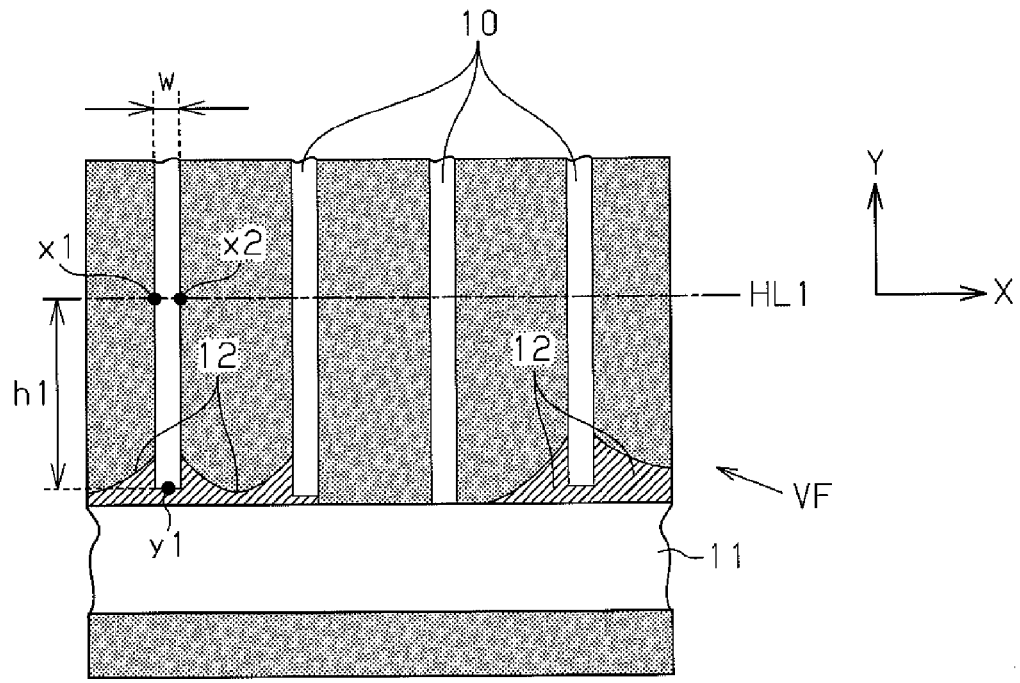
FIGS. 8(a) and 8(b) are diagrams showing the thickness, height, and quantity of the electrode plates that are used for calculations.

The process for obtaining the thickness, quantity, and height of the electrode plates 10 when the reference horizontal line is based on the flange will now be described with reference to FIG. 8(a). In this case, the computer terminal 31 obtains the grayscale of the front lighting image VF on the reference horizontal line HL1 in the X direction to specify the position of a changing point x1 at which black changes to white and the position of a changing point x2 at which white changes to black. The computer terminal 31 obtains the distance in the X direction from the changing point x1 to the changing point x2 as the thickness w of the electrode plate 10.

Further, the computer terminal 31 specifies each electrode plate 10 and obtains the quantity of the electrode plates 10. The computer terminal 31 also obtains the grayscale of the front lighting image VF along each electrode plate 10 to specify a changing point y1 at which white changes to black as the lower end of that electrode plate 10. A distance h1 in the Y direction from the reference horizontal line HL1 to the changing point y1 is obtained as the height of the electrode plate 10.

Figure 8B:
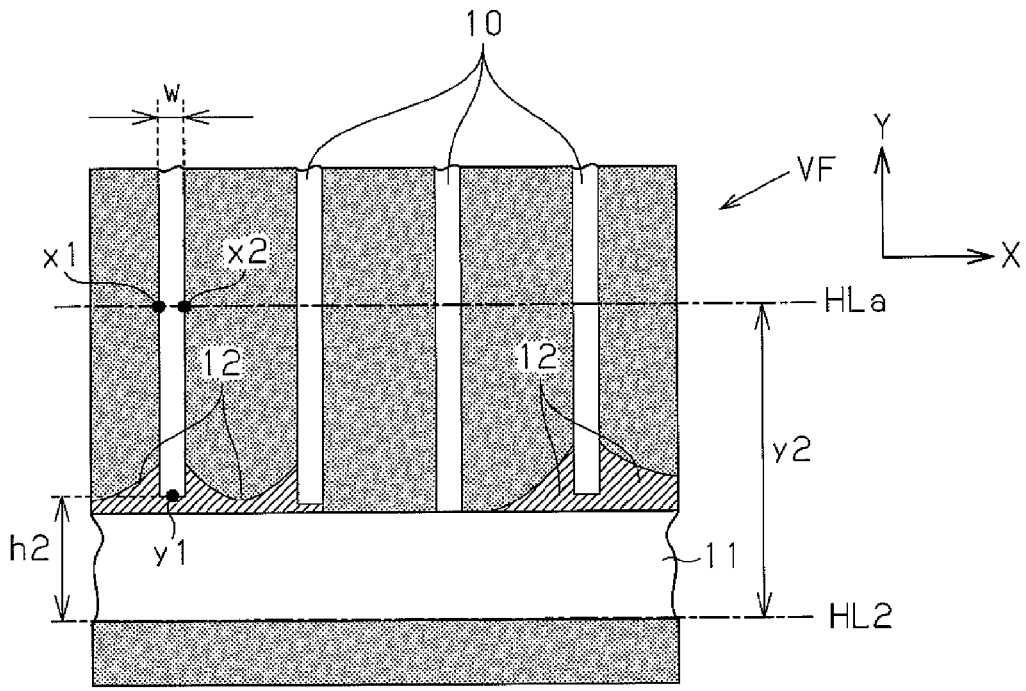

The process for obtaining the thickness, quantity, and height of the electrode plates 10 when the reference horizontal line is based on the current collector plate surface will be now be described with reference to FIG. 8(b). In this case, the computer terminal 31 sets a line HLa, which is shifted upward in parallel from the reference horizontal line HL2 by a specified dimension y2, obtains the grayscale of the front lighting image VF on the line HLa in the X direction to specify the position of the changing point x1 at which black changes to white and a position of the changing point x2 at which white changes to black. The computer terminal 31 obtains the distance in the X direction from the changing point x1 to the changing point x2 as the thickness w of the electrode plate 10. The computer terminal 31 specifies each electrode plate 10 and obtains the quantity of the electrode plates 10. The computer terminal 31 calculates the grayscale of the front lighting image VF along each electrode plate 10 to specify the changing point y1 at which white changes to black as the lower end of that electrode plate 10. A distance h2 in the Y direction from the reference horizontal line HL2 to the changing point y1 is obtained as the height of the relevant electrode plate 10.

In step S190, the computer terminal 31 determines the appropriateness of the obtained thickness and quantity of the electrode plates. If the thickness of each electrode plate 10 or the quantity of the electrode plates 10 is inappropriate, the computer terminal 31 outputs an "electrode plate NG signal" and immediately terminates the present inspection. Even if the thickness and the quantity of the electrode plates are appropriate, if an electrode plate 10 has an inappropriate height, in step S200, the computer terminal 31 outputs an "electrode plate height NG signal" and immediately terminates the present inspection.

If the thickness, quantity, and height of the electrode plates 10 are all appropriate, the computer terminal 31 performs a fillet thickness inspection in step S210. The thickness of a fillet 12 refers to the distance from the current collector plate surface to the lowest part in the upper surface of the fillet 12. The thickness of each fillet 12 is based on the height of each electrode plate 10 obtained in step S180. In the preferred embodiment, the fillet thickness is ultimately obtained and determined from the front lighting image VF.

The computer terminal 31 determines the appropriateness of the thickness of each fillet 12 in the step S220. If the fillet thickness of the each fillet 12 is appropriate, the computer terminal 31 outputs an "OK signal" indicating that the connection of each electrode plate 10 to the current collector plate 11 in the electrode plate-connected structure is satisfactory and then terminates the present inspection.

If there is a fillet 12 with an inappropriate thickness (S220: NG), in step S230, the computer terminal 31 inspects the shape of that fillet 12. The shape inspection will now be discussed below.

Figure 9A:
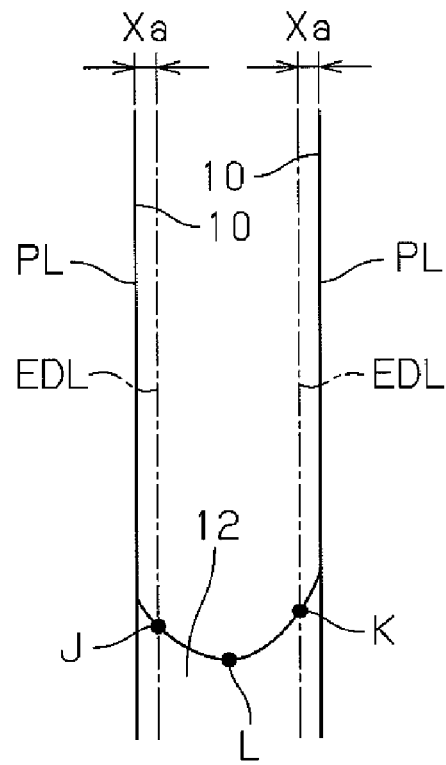
FIGS. 9(a) and 9(b) are diagrams illustrating shape determination of the fillet.
Figure 9B:
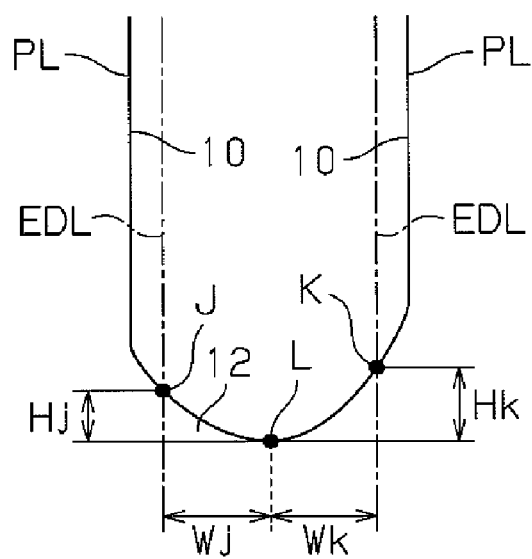
Figure 10:
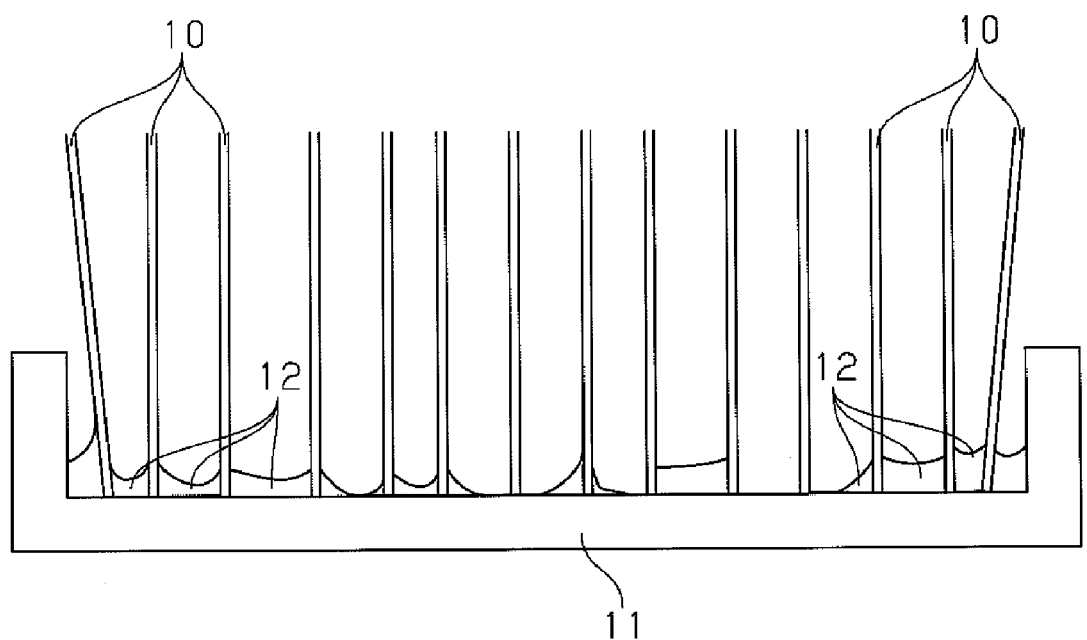
FIG. 10 is a partially enlarged side view showing a side surface of a rechargeable battery electrode plate-connected structure.

FIGS. 9(a) and (b) show the connection portion between the current collector plate 11 and two adjacent electrode plates 10. First, the computer terminal 31 sets an electrode plate line PL along the major surface of each of two electrode plates 10 located on opposites sides of the fillet 12. The detection of the major surface of each electrode plate 10 for setting the electrode plate line PL may be performed using the front lighting image VF. Thereafter, the computer terminal 31 sets a shape edge detection line EDL for each electrode plate line PL. The shaped edge detection line EDL is inwardly spaced apart from the corresponding electrode plate line PL by a predetermined distance xa. The grayscale is obtained from the lower side to the upper side along each shape edge detection line EDL in the back lighting image VB, and edge points J and K, which are the changing point where black changes to white, are specified.

The computer terminal 31 then obtains the position of the lowermost point L in the upper surface of the fillet 12 relative to the edge points J and K. The lowermost point L has already been obtained when obtaining the thickness of the fillet 12. The relative position, specifically, the XY coordinates of the lowermost point L, the edge point J, and the edge point K are relatively specified as (x1, y1), (xj, yj), and (xk, yk). A distance Hj in the Y direction between the lowermost point L and the edge point J and a distance Hk in the Y direction between the lowermost point L and the edge point K are obtained from equations (1) and (2). A distance Wj in the X direction between the lowermost point L and the edge point J and a distance Wk in the X direction between the lowermost point L and the edge point K are obtained from equations (3) and (4).

$$Hj = yj - y1 \tag{1}$$

$$Hk = yk - y1 \tag{2}$$

$$Wj = x1 - xj \tag{3}$$

$$Wk = xk - x1 \tag{4}$$

In step S240, the computer terminal 31 evaluates the inspected shape of the fillet 12 that has an insufficient thickness. In the shape inspection determination, the computer terminal 31 determines whether or not the fillet 12 has an appropriate shape for ensuring sufficient connection strength based on each of the distances Hj, Hk, Wj, and Wk. Specifically, if the distances Hj and Hk in the Y direction each exceed a reference value, the fillet 12 is sufficiently bulged and adhered with the electrode plates 10 on both sides of the fillet 12. Thus, it is determined that the fillet 12 has sufficient connection strength. If the distances Wj and Wk in the X direction respectively each exceed a reference value, the lowermost point L of the fillet 12 is not biased toward and close to the electrode plate 10 on one side of the fillet 12. Thus, it is determined that the fillet 12 has sufficient connection strength.

Accordingly, the computer terminal 31 determines that the connection strength of the fillet 12 is sufficient if at least any one of a condition in which the distances Hj and Hk in the Y direction both exceed the reference value or a condition in which the distances Wj and Wk in the X direction both exceed the reference value is satisfied. In this case, the computer terminal 31 outputs an "OK signal" and terminates the present inspection. If none of the above conditions is satisfied, the computer terminal 31 determines a fillet is missing, outputs a "fillet missing state NG signal," and terminates the present inspection.

After inspecting one of the two electrode plate-connected structures in the pair of electrode plate-connected structures 22, the other one of the electrode plate-connected structures is inspected in the same manner.

The computer terminal 31 corresponds to an inspection circuit.

In the preferred embodiment, the inspection apparatus and the inspection method of the rechargeable battery electrode plate-connected structure have the advantages described below.

(1) The inspection apparatus includes the imaging device 25 arranged on one side of the rechargeable battery electrode plate-connected structure. The inspection apparatus includes two lighting devices, the first lighting device 26, which is arranged on the same side of the electrode plate-connected structure as the imaging device 25, for irradiating the electrode plate-connected structure with inspection light, and the second lighting device 27, which is arranged facing the imaging device 25 with the electrode plate-connected structure located in between, for irradiating the electrode plate-connected structure with inspection light. To inspect the connection state of the fillets, the computer terminal 31 of the inspection apparatus analyzes two images, the front lighting image VF, captured by the imaging device 25 in a state in which only the first lighting device 26 is lit, and the back lighting image VB, captured by the imaging device 25 in a state in which only the second lighting device 27 is lit.

In other words, in the preferred embodiment, the rechargeable battery electrode plate-connected structure is lit from one side, and the front lighting image in which the connection portion between each electrode plate 10 and the current collector plate 11 is captured at the lit side is acquired. Further, the rechargeable battery electrode plate-connected structure is lit from another side, and the back lighting image imaging in which the connection portion between each electrode plate 10 and the current collector plate 11 is captured at the side opposite to the lit side is acquired. The two acquired images are analyzed to inspect the connection state of the fillets 12.

In the back lighting image VB, if the inspection light is shielded due to a bent electrode plate 10, this would form a shadow and hide the corresponding fillet 12. Although the fillet 12 in the shadowed portion can be detected by raising the illuminance of the second lighting device 27, this would cause halation of the light and blur the electrode plate 10. In this regards, in the preferred embodiment, when inspecting the connection state of the fillets, the front lighting image VF captured by the lighting of the first lighting device 26 located at the side of the imaging device 25 is used in addition to the back lighting image VB. Thus, the connection state of the fillet 12 formed at the connection portion between each electrode plate 10 and the current collector plate 11 is more accurately inspected by obtaining the positions of the electrode plates 10 from the front lighting image VF and capturing the back lighting image VB with the second lighting device 27 having an increased illuminance. This reduces erroneous determinations and eliminates additional tasks such as re-inspection when such an erroneous determination is made.

Figure 11:
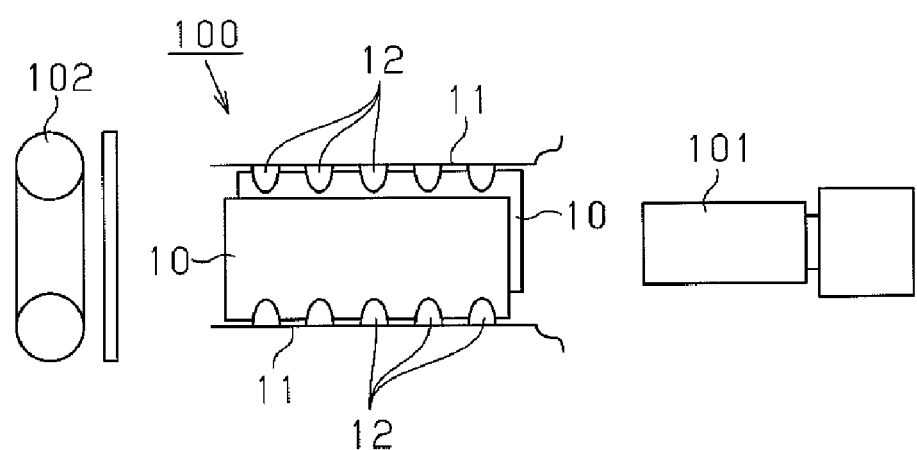
FIG. 11 is a schematic diagram of an inspection apparatus in the prior art.

(2) In the preferred embodiment, the computer terminal 31 performs an inspection by obtaining the position of each electrode plate 10 from the front lighting image VF and the shape of each fillet 12 from the back lighting image VB. In this case, since the position of each electrode plate 10 is obtained from the front lighting image VF, the inspection is can be conducted without any problems even if the electrode plates 10 become blurred in the back lighting image VB when the halation of light occurs due to an increase in the illuminance of the second lighting device 27. The simultaneous use of the first lighting device 26 and the second lighting device 27 allows the illuminance of the second lighting device 27 when capturing the back lighting image VB to be raised to a higher level compared to the lighting device (e.g., lighting device 102 of FIG. 11) of the conventional inspection apparatus. Thus, the shapes of the fillets 12 are more accurately obtained.

(3) In the preferred embodiment, the computer terminal 31 checks the quantity of the fillets 12 from the quantity of the fillet cutout frames FF, each using the surfaces of the adjacent electrode plates 10 as first and second sides and the upper surface of the fillet 12 as the lower side. When setting the fillet cutout frame FF, the computer terminal 31 obtains the positions of the first and second sides of the fillet cutout frame FF from the front lighting image VF and obtains the position of the lower side of the fillet cutout frame FF from the back lighting image VB. As described above, when capturing the back lighting image VB, although the shape of the fillet 12 would be more accurately detected by raising the illuminance of the second lighting device 27, this would cause halation of the light and blur the electrode plate 10. In this regards, in the preferred embodiment, the fillet cutout frame FF is set by obtaining the positions of the surfaces of the adjacent electrode plates 10 from the front lighting image VF and obtaining the upper surface of the fillet 12 from the back lighting image VB. Thus, the fillet cutout frame FF is set by accurately detecting both the position of the electrode plate 10 and the shape of the fillet 12. Thus, the checking of the quantity of the fillets 12 when inspecting the connection state of the fillets 12 is more accurately performed.

(4) In the preferred embodiment, the computer terminal 31 checks the thickness, the quantity, and the height of the electrode plates 10 from the positions of the electrode plates 10 obtained from the front lighting image VF. As described above, the position of each electrode plate 10 is accurately determined by using the front lighting image VF. The thickness, quantity, and height of the electrode plate 10 checked when inspecting the connection state of the fillets 12 is thus accurate.

(5) In the preferred embodiment, the computer terminal 31 obtains the thickness of each fillet 12 from the front lighting image VF and determines the appropriateness of the fillet thickness. More specifically, the thickness of the fillet 12 is obtained from height data of the electrode plates 10 taken from the front lighting image VF. By using the front lighting image VF in which the position of each electrode plate 10 is more accurately obtained, the height of the electrode plate 10 when inspecting the connection state of the fillet 12 and the thickness of the fillet 12 during the inspection are obtained more accurately.

(6) In the preferred embodiment, the position of the reference horizontal line HL1, which is the reference line in the thicknesswise direction of the fillet 12, is obtained from the back lighting image VB. If the illuminance of the inspection light emitted from the second lighting device 27 is raised, the positions of the electrode plates 10 becomes unclear in the back lighting image VB, but the outline of other portions become clear. Thus, by determining the position of the reference horizontal line HL1 from the back lighting image VB, the position of the reference horizontal line HL1 is more accurately obtained. Furthermore, the connection state of the fillets 12 is more accurately inspected using the reference horizontal line HL1 as the reference position in the thicknesswise direction of the fillet 12.

It should be apparent to those skilled in the art that the present invention may be embodied in many other specific forms without departing from the spirit or scope of the invention. Particularly, it should be understood that the present invention may be embodied in the following forms.

In the above-described embodiment, the first lighting device 26 and the second lighting device 27 use an LED as a light emitting body. However, a light emitting body other than the LED such as an fluorescent lamp may be used as the light emitting body of the lighting device.

The details for obtaining the reference horizontal line, the fillet cutout images, the thickness, quantity, and height of the electrode plates, and the fillet thickness inspection and shape inspection are not limited as described in the above-described embodiment and may be changes as required. One or more steps in the inspection procedures may be omitted when unnecessary. It is only necessary that the shape of the fillets 12 be obtained using the back lighting image VB and the position of each electrode plate 10 be obtained using the front lighting image VF when inspecting the connection state of the fillets so that the illuminance of light can be raised when capturing the back lighting image VB without having to take into consideration degradation in the captured image of the electrode plates 10 due to the halation of the light. As a result, the fillet shape can be more accurately obtained, and the inspection of the connection state of the fillet 12 can be more accurately performed.

The detailed portions of the inspection apparatus in the above-described embodiment may be changed when necessary. It is only necessary that the inspection apparatus includes the imaging device 25 arranged on one side of the rechargeable battery electrode plate-connected structure, the first lighting device 26 arranged on the same side of the electrode plate-connected structure as the imaging device 25, and the second lighting device 27 arranged facing the imaging device 25 with the electrode plate-connected structure in between so that the back lighting image VB and the front lighting image VF can be captured. The two images are analyzed to inspect the connection state of the fillet so that more accurate inspection can be performed.

The present examples and embodiments are to be considered as illustrative and not restrictive, and the invention is not to be limited to the details given herein, but may be modified within the scope and equivalence of the appended claims.

What is claimed is:

1. An inspection apparatus for a rechargeable battery electrode plate-connected structure including a plurality of electrode plates, each having a connecting end portion to be connected to a current collector plate by a fillet, wherein the inspection apparatus is for inspecting a connection state of a fillet formed at a connection portion between each connecting end portion and the current collector plate, the inspection apparatus comprising:
   an imaging device arranged on one side of the rechargeable battery electrode plate-connected structure;
   a first lighting device which emits inspection light to the rechargeable battery electrode plate-connected structure, with the first lighting device being arranged on the one side of the rechargeable battery electrode plate-connected structure;
   a second lighting device which emits inspection light to the rechargeable battery electrode plate-connected structure, with the second lighting device facing the imaging device so that the rechargeable battery electrode plate-connected structure is located between the second lighting device and the imaging device; and
   an inspection circuit connected to the imaging device, wherein the inspection circuit inspects the connection state of the fillet by analyzing a front lighting image of the rechargeable battery electrode plate-connected structure, which is captured by the imaging device when only the first lighting device emits the inspection light, and a back lighting image of the rechargeable battery electrode plate-connected structure, which is captured by the imaging device receiving the inspection light of the second lighting device passing through gaps between the electrode plates and the current collector plate when only the second lighting device emits the inspection light, and wherein the inspection circuit detects the positions of the plurality of electrode plates by analyzing the front lighting image that is captured by the imaging device receiving the inspection light emitted from the first lighting device and reflected at illuminated side surfaces of the electrode plates and the current collector plate when only the first lighting device emits the inspection light.

2. The inspection apparatus according to claim 1, wherein the inspection circuit plurality obtains the shape of each fillet by analyzing a back lighting image.

3. The inspection apparatus according to claim 1, wherein:
   the inspection apparatus obtains the quantity of rectangular fillet cutout frames, each of which includes first and second sides respectively corresponding to two opposing major surfaces of two adjacent electrode plates and a lower side corresponding to an upper surface of a fillet, and determines the quantity of the fillets from the quantity of fillet cutout frames; and
   the inspection circuit obtains the positions of the first and the second sides of the fillet cutout frame using the front lighting image and the position of the lower side of the fillet cutout frame using the back lighting image.

4. The inspection apparatus according to claim 1, wherein the inspection circuit obtains at least one of the thickness of each electrode plate, the quantity of the electrode plates, and the height of each electrode plate from the positions of the plurality of electrode plates using the front lighting image.

5. The inspection apparatus according to claim 1, wherein the inspection circuit obtains the thickness of the fillet from the current collector plate using the front lighting image and determines appropriateness of the obtained thickness of the fillet.

6. The inspection apparatus according to claim 1, wherein the inspection circuit obtains the position of a reference line in a thicknesswise direction of the fillet using the back lighting image.

7. A method for inspecting a rechargeable battery electrode plate-connected structure including a plurality of electrode plates, each having a connecting end portion to be connected to a current collector plate by a fillet, in which a connection state of a fillet formed at a connection portion between each connecting end portion and the current collector plate is inspected, the method comprising:
   illuminating, with the inspection light emitted from a first lighting device, one side of the rechargeable battery electrode plate-connected structure and capturing an image of the connection portion between each electrode plate and the current collector plate at a position facing toward the illuminated side of the rechargeable battery electrode plate-connected structure to acquire a front lighting image of the rechargeable battery electrode plate-connected structure;
   illuminating, with the inspection light emitted from a second lighting device, the rechargeable battery electrode plate-connected structure from the other side of the rechargeable battery electrode plate-connected structure and capturing an image of the connection portion between each electrode plate and the current collector plate at a position facing toward a side of the rechargeable battery electrode plate-connected structure opposite the illuminated side by receiving the inspection light of the second lighting device passing through gaps between the electrode plates and the current collector plate to acquire a back lighting image of the rechargeable battery electrode plate-connected structure; and inspecting the connection state of the fillet by analyzing both the front lighting image and the back lighting image of the rechargeable battery electrode plate-connected structure, wherein the inspecting includes detecting the positions of the plurality of electrode plates by analyzing the front lighting image that is captured by receiving the inspection light emitted from the first lighting device and reflected at illuminated side surfaces of the electrode plates and the current collector plate when only the first lighting device emits the inspection light.

8. The inspection method according to claim 7, wherein said inspecting includes detecting each fillet from the back lighting image.

9. The inspection method according to claim 7, wherein said inspecting step includes:

obtaining the quantity of rectangular fillet cutout frames, each of which includes first and second sides respectively corresponding to two opposing major surfaces of two adjacent electrode plates and a lower side corresponding to an upper surface of a fillet, and determining the quantity of the fillets from the quantity of fillet cutout frames; and obtaining the positions of the first and the second sides of the fillet cutout frame using the front lighting image, and obtaining the position of the lower side of the fillet cutout frame using the back lighting image.

10. The inspection method according to claim 7, wherein said inspecting includes obtaining at least one of the thickness of each electrode plate, the quantity of the electrode plates, and the height of each electrode plate from the positions of the plurality of electrode plates using the front lighting image.

11. The inspection method according to claim 7, wherein said inspecting includes obtaining thickness of the fillet from the current collector plate using the front lighting image and determining appropriateness of the obtained thickness of the fillet.

12. The inspection method according to claim 7, wherein said inspecting step includes obtaining the position of a reference line in a thicknesswise direction of the fillet using the back lighting image.

\* \* \* \* \*